US006120537A

United States Patent [19]
Wampler

[11] Patent Number: 6,120,537
[45] Date of Patent: *Sep. 19, 2000

[54] SEALLESS BLOOD PUMP WITH MEANS FOR AVOIDING THROMBUS FORMATION

[75] Inventor: Richard K. Wampler, Granite Bay, Calif.

[73] Assignee: Kriton Medical, Inc., Sacramento, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/996,577

[22] Filed: Dec. 23, 1997

[51] Int. Cl.[7] .............................. A61M 1/12; F01D 25/00
[52] U.S. Cl. .................... 623/3.14; 415/229; 417/423.12
[58] Field of Search .................................. 623/3; 600/16, 600/17; 417/423.12, 423.13; 415/229, 900; 601/153

[56] References Cited

U.S. PATENT DOCUMENTS

| | | |
|---|---|---|
| 2,725,266 | 11/1955 | Mendelsohn . |
| 3,487,784 | 1/1970 | Rafferty et al. . |
| 3,493,274 | 2/1970 | Emslie et al. . |
| 3,957,389 | 5/1976 | Rafferty et al. . |
| 4,057,369 | 11/1977 | Isenberg et al. . |

(List continued on next page.)

FOREIGN PATENT DOCUMENTS

| | | |
|---|---|---|
| 393 457 | 10/1991 | Australia . |
| 611580 | 8/1994 | European Pat. Off. . |
| 847767 | 6/1998 | European Pat. Off. . |
| 2-176199 | 7/1990 | Japan ...................................... 415/229 |

OTHER PUBLICATIONS

Tanaka et al., "A New Seal–Less Centrifugal Blood Pump", Japan Journal of Artificial Organs. 14 (3), pp. 1126–1129, (1985).

Nishida et al., "Development of the Terumo Capiox Centrifugal Pump and Its Clinical Application to Open Heart Surgery: A Comparative Study with the Roller Pump", pp. 24–28, (1992).
Kijima et al., "A Straight Path Centrifugal Blood Pump Concept in the Capiox Centrifugal Pump", pp. 32–37 (1993).
Yamane et al. "Fundamental Characteristics of Magnetically Suspended Centrifugal Blood Pump", pp. 130–131 (1994).
Kijima et al., "The Margin of Safety in the Use of a Straight Path Centrifugal Blood Pump", Artificial Organs, 18(9), pp. 680–686 (1994).
"Implantable Artificial Cardiac Blood Pump Prototype Developed", Medical Equipment Journal of Japan, (May 1994).
Yamane et al. "Design of a Centrifugal Blood Pump with Magnetic Suspension", 1 page, Abstract (Sept. 1994), 2nd Congress of the International Society for Rotary Blood Pumps.
Yamane et al., "Design of a Centrifugal Blood Pump with Magnetic Suspension", Artificial Organs, 19(7) pp. 625–630, (1995).
Akamatsu et al., "Recent Studies of the Centrifugal Blood Pump with a Magnetically Suspended Impeller", Artificial Organs, 19(7), pp. 631–634, (1995).
Yamane "Performance Improvements of a Centrifugal Blood Pump with Mono–Pivot Magnetic Suspension", pp. 538–539 (1996).

Primary Examiner—David H. Willse
Attorney, Agent, or Firm—Gerstman, Ellis & McMillin, Ltd.

[57] ABSTRACT

A blood pump comprising: a pump housing, and a rotor mounted for rotation within the housing. The rotor has a rotational axis and an attached impeller. The blood pump has a blood flow path that passes about the rotor, with the rotor having a peripheral edge surrounding an end face. The end face has a profiled surface that augments blood flow radially outwardly from a central portion of the end face toward the peripheral edge as the rotor rotates when compared with a flat end face.

20 Claims, 9 Drawing Sheets

U.S. PATENT DOCUMENTS

| | | |
|---|---|---|
| 4,072,370 | 2/1978 | Wasson . |
| 4,135,253 | 1/1979 | Reich et al. . |
| 4,253,798 | 3/1981 | Sugiura . |
| 4,382,245 | 5/1983 | Harrigan . |
| 4,507,048 | 3/1985 | Belenger et al. .......................... 415/90 |
| 4,625,712 | 12/1986 | Wampler . |
| 4,688,998 | 8/1987 | Olsen et al. . |
| 4,704,121 | 11/1987 | Moise . |
| 4,745,345 | 5/1988 | Petersen . |
| 4,763,032 | 8/1988 | Bramm et al. . |
| 4,779,614 | 10/1988 | Moise . |
| 4,789,251 | 12/1988 | McPherson et al. . |
| 4,806,080 | 2/1989 | Mizobuchi et al. . |
| 4,846,152 | 7/1989 | Wampler et al. . |
| 4,908,012 | 3/1990 | Moise et al. . |
| 4,944,748 | 7/1990 | Bramm et al. . |
| 4,957,504 | 9/1990 | Chardack . |
| 4,976,729 | 12/1990 | Holfert et al. . |
| 4,994,017 | 2/1991 | Yozu . |
| 5,017,103 | 5/1991 | Dahl . |
| 5,049,134 | 9/1991 | Golding et al. . |
| 5,055,005 | 10/1991 | Kletschka . |
| 5,078,741 | 1/1992 | Bramm et al. . |
| 5,092,879 | 3/1992 | Jarvik . |
| 5,106,263 | 4/1992 | Irie . |
| 5,112,200 | 5/1992 | Isaacson et al. . |
| 5,112,202 | 5/1992 | Oshima et al. . |
| 5,147,388 | 9/1992 | Yamazaki . |
| 5,149,253 | 9/1992 | Miyamoto et al. . |
| 5,160,246 | 11/1992 | Horiuchi . |
| 5,182,533 | 1/1993 | Ritts . |
| 5,195,877 | 3/1993 | Kletschka . |
| 5,201,642 | 4/1993 | Hinckley . |
| 5,211,546 | 5/1993 | Isaacson et al. ......................... 417/356 |
| 5,282,849 | 2/1994 | Kolff et al. . |
| 5,290,236 | 3/1994 | Mathewson . |
| 5,302,091 | 4/1994 | Horiuchi . |
| 5,306,295 | 4/1994 | Kolff et al. . |
| 5,316,440 | 5/1994 | Kijima et al. ........................... 415/206 |
| 5,324,177 | 6/1994 | Golding et al. . |
| 5,342,825 | 8/1994 | Iannello et al. . |
| 5,370,509 | 12/1994 | Golding et al. . |
| 5,385,581 | 1/1995 | Bramm et al. . |
| 5,392,881 | 2/1995 | Cho et al. . |
| 5,397,349 | 3/1995 | Kolff et al. . |
| 5,397,953 | 3/1995 | Cho . |
| 5,399,074 | 3/1995 | Nose et al. ........................... 417/423.1 |
| 5,441,535 | 8/1995 | Takahashi et al. . |
| 5,443,503 | 8/1995 | Yamane . |
| 5,470,208 | 11/1995 | Kletschka . |
| 5,507,629 | 4/1996 | Jarvik . |
| 5,527,159 | 6/1996 | Bozeman, Jr. et al. . |
| 5,569,111 | 10/1996 | Cho et al. . |
| 5,575,630 | 11/1996 | Nakazawa et al. ..................... 417/420 |
| 5,588,812 | 12/1996 | Taylor et al. . |
| 5,601,418 | 2/1997 | Ohara et al. . |
| 5,607,329 | 3/1997 | Cho et al. . |
| 5,613,935 | 3/1997 | Jarvik . |
| 5,649,811 | 7/1997 | Krol, Jr. et al. . |
| 5,695,471 | 12/1997 | Wampler . |

SEALLESS BLOOD PUMP WITH MEANS FOR AVOIDING THROMBUS FORMATION

BACKGROUND OF THE INVENTION

The invention relates generally to the field of blood pumps, and particularly continuous flow pumps of rotary design suitable for permanent implantation in humans, for use as chronic ventricular assist devices.

Thousands of heart patients who suffer from severe left ventricular heart failure could benefit from cardiac transplantation. However, owing to a shortage of donor hearts, most of these patients face a foreshortened life span characterized by frequent hospitalizations, severe physical disability, and death from congestive failure or cardiogenic shock. With the use of an effective left ventricular assist device on a chronic basis, many of these patients could be returned to prolonged and productive lives.

Such a left ventricular assist device is particularly shown in my prior copending application Ser. Nos. 08/603,536 and 08/910,375, which disclose pumps of rotary, continuous flow design rather than of a pulsatile flow design. The disclosed rotary blood pumps solve numerous clinical problems and have significant advantages for use as a left ventricular assist device, eliminating the necessity for a drive shaft seal and having axial thrust bearings which are regularly washed by fresh blood flow to prevent thrombosis from occurring.

However, it would be desirable to increase the blood flow across the end of the rotor of such rotary pumps, and rotary pumps of other designs, to further reduce the possibilities of clotting where low blood flow occurs at stagnation points such as areas of the pump rotor end near the axis of rotation.

DESCRIPTION OF THE INVENTION

By this invention a blood pump is provided which comprises a pump housing and a rotor mounted for rotation within said housing, the rotor having a rotational axis and an attached impeller. The blood pump has a blood flow path that passes about the rotor, with the rotor having a peripheral edge defining an end face. The end face has a profiled surface that augments blood flow radially outwardly from a central portion of the end face toward the peripheral edge as the rotor rotates, when compared with a nonprofiled, flat end face. Thus, in particular, a sealless blood pump where flowing blood surrounds the rotor in operation can exhibit improved circulation of blood across the end face of the rotor by means of the profiled surface of this invention. This can be used even when a thrust bearing or other kind of bearing is provided at the same end of the rotor, particularly when the rotor translates a small distance back and forth in an axial direction while rotating, as taught in the previously described patent applications.

Preferably, the profiled surface on the end of the rotor comprises a channel which extends from the central portion of the end face, to provide a flow channel and augmented blood flow radially outwardly from the rotor end as the rotor rotates in use.

The channel may extend outwardly in a plurality of directions, typically two different directions extending toward the peripheral edge from the central portion of the end face. However, if desired, a branching channel having three, four, or more legs which extend radially outwardly from the center may be used.

Typically, the channel extends toward the peripheral edge in at least a pair of spaced positions. The channel at a first of these positions may define an angle with the adjacent peripheral edge which is different from the angle between the channel and the adjacent peripheral edge at a second of the positions. In other words, the channel at the first position may be substantially perpendicular to the peripheral surface at that point. However, the channel at the second of the spaced positions may approach the periphery at an acute angle of typically 60° or the like, so that differing angularity of the channel ends is provided, causing an asymmetry of flow characteristics upon rotation of the end face.

Alternatively, the channel may have a closed end at a central portion of the end face, so that flow upon rotation of the rotor is unidirectional through the channel from the central portion toward the peripheral, open end of the channel.

It is also desirable in some circumstances for at least one conduit to extend through the rotor between the channel and a surface of the rotor that is spaced from the end face, to enhance blood circulation across the end face.

As another alternative, the profiled surface at the end of the rotor may comprise a projecting rib which extends from a central portion of the end face outwardly to or toward the peripheral edge. This also will augment the flow of blood upon rotation of the rotor from central portions of the rotor end toward the periphery thereof.

The pump housing typically comprises an elongated inlet tube at one end and an impeller casing portion on another end, with the impeller casing portion including a discharge tube, so that blood flow enters the pump through the inlet tube and exits the pump through the discharge tube.

The rotor may have an elongated shaft portion, with the impeller being attached to the shaft portion at a position located within the impeller casing portion. A primary flow channel for blood is provided by an annular space or volume between the shaft portion and the housing.

The end face of the blood pump rotor may define a thrust bearing for restraining the rotor from translating past a predetermined position along its longitudinal axis. The thrust bearing may comprise mating bearing surfaces which are respectively carried by the rotor and the pump housing. The profiled surface may comprise a channel extending within the thrust bearing from the central portion of the end face outwardly across the peripheral edge as previously described.

A motor stator may be positioned within the housing adjacent the impeller for producing an electromagnetic field.

Broadly, the profiled surface of the rotor end face defines a flow recess which occupies a position that at least nearly intersects the rotational axis. The recess permits radially outward flow in the recess as the rotor rotates.

Thus, blood pumps of the type described in the previously cited patent applications may be improved by the profiled surface on the end of the rotor, to eliminate a stagnant area which is found in rotors having flat ends, where blood flows only slowly and thus is more subject to clotting. The invention may also be used with other types of rotary blood pumps as well.

DETAILED DESCRIPTION OF THE PREFERRED EMBODIMENT

Turning now to FIGS. 1–11 of the drawings, a sealless rotary blood pump 11 includes a housing 12, having an elongated inlet tube 13 and an impeller casing or volute 14. A discharge tube 16 extends through the housing to communicate with the interior periphery of casing 14. Tube 16 has a tangential orientation with respect to a radius of the casing, for effectively channeling the blood output from the pump.

A pump rotor 17 is located within housing 12, within casing 14, and includes an elongated, right-circular cylindrical support shaft or spindle 18, attached to a disc-shaped impeller 19. Rotor 17 is mounted for rotation about a longitudinal axis which extends both through shaft 18 and impeller 19. It should be noted that the preferred embodiment disclosed herein includes an impeller and a casing of centrifugal design. However, many of the structural features and aspects of operation of the present invention may also be adapted advantageously to rotary blood pumps of axial flow design.

The pump 11 of the present invention includes a forward magnetic bearing 21 and a rearward magnetic bearing 22 (FIG. 8) to levitate rotor 17 and maintain it in proper radial alignment with respect to its longitudinal axis. A radial magnetic bearing construction is shown in U.S. Pat. No. 4,072,370, issued to Wasson. The '370 Patent is hereby expressly incorporated by reference. The forward magnetic bearing 21 herein may be constructed entirely in accordance with the teachings of the '370 Patent. However, several simplifications and improvements to the construction shown in the '370 Patent are disclosed herein. For example, it has been determined that the radially polarized ring magnets (numerals 44 and 46) of the '370 device, are not necessary for successful practice of the invention herein. In addition, as will be explained below, the axially magnetized ring magnets (numeral 22) of the '370 device may advantageously be replaced with axially magnetized disc magnets for purposes of the present invention.

Accordingly, the forward magnetic bearing 21 includes a plurality of rings, comprising ferromagnetic pole pieces 23 and axially polarized permanent magnets 24. As shown most clearly in FIGS. 7 and 8, pole pieces 23 and magnets 24 are arranged in contingent, alternating fashion, and are located between outer sidewall 26 and inner sidewall 27 of inlet tube 13. The polarization of opposing magnets is the same, inducing an identical polarization into a respective pole piece therebetween. A combination of high strength adhesive and surrounding tube sidewalls maintains the arrangement of magnets and pole pieces in contingent relation, despite strong magnet forces attempting to urge the rings apart.

Forward magnetic bearing 21 also includes a plurality of discs, comprising ferromagnetic pole pieces 28 and axially polarized permanent magnets 29. Pole pieces 28 and magnets 29 are also arranged in contingent, alternation fashion, so as to form a magnetic structure which mirrors the polarity and axial position of respective pieces and magnets of the surrounding rings. This magnetic structure is first assembled and secured together using high strength adhesive, and is then installed within the hollow volume of shaft or spindle 17. The magnetic polarizations and repulsive forces produced by the magnets and the pole pieces of forward magnetic bearing 21 are such that magnetic levitation of support shaft 18 results.

To provide additional radial restraint for rotor 17, rearward magnetic bearing 22 is also provided. Bearing 22 includes a first ring magnet 31 mounted on an outer wall of casing 14, and a second ring magnet 32 imbedded within a circular casing base 33. The bottom portion of casing 14 is attached and sealed to base 33, to form a fluid impervious enclosure for impeller 19 (see FIG. 7). Both magnets 31 and 32 are axially polarized, but each has a different polarization facing impeller 19. Bearing 22 also includes a plurality of rod magnets 34, transversely extending from an upper face portion 36 to a lower face portion 37 of impeller 19. Rod magnets 34 are arranged in spaced, circular fashion, adjacent an outer periphery 38 of impeller 19. The polarizations between the ends of magnets 34 and the adjacent surfaces of magnets 31 and 32 are respectively opposite, creating attractive, but equal and opposite magnetic forces acting on the impeller. It can be seen that radial movement of the impeller (deflection from the axis of rotation) will result in a restoring force due to the attraction between the magnets 34 towards magnets 31 and 32. The magnetic force in the axial direction will largely be counterbalanced to the opposing magnetic attraction of magnets 34 to magnet 31 and magnets 34 to magnet 32. However, the action of the magnetic force in the axial direction would not be restoring.

It should also be noted that other configurations, locations, numbers, and polarization orientations may be used for the components forming rearward magnetic bearing 22. For example, magnets 34 may be arcuate segments, rather than rods. Also, the polarizations of the magnets 31, 32, arid 34 may be arranged to effect respective repulsive forces, rather than the attractive forces specifically disclosed herein.

Although the drawings show magnets 32 and 34 as if portions thereof are directly immersed in blood, in actual practice, a thin-walled non-magnetic jacket or a plastic coating would be placed over these portions, to prevent contact between the magnets and the blood. Such contact, if it were allowed, would likely cause an undesirable reaction, to the detriment of the blood. However, for clarity, the referenced jacket or coating is not shown in the drawings.

To provide mechanical limitations on axial, translational excursions of the rotor, a first thrust bearing 39 and a second thrust bearing 41 are provided. First thrust bearing 39 includes a threaded plug 42, installed within casing base 33. Plug 42 is screw adjustable along the longitudinal axis of rotor 17, and includes a recessed bearing surface 43. Surface 43 is contoured to accommodate a corresponding bearing tip 44, in the lower face portion of impeller 14. It should be noted that the particular configuration of bearing 39 is not critical, and planar bearing surfaces may alternatively be used in this application.

Second thrust bearing 41 is secured within the blood entry end of inlet tube 13, and includes a spider 46, adjustment knob 47, and ball 48. Rotation of knob 47 will translate ball 48 along the longitudinal axis of rotor 17.

Alternative locations and constructions for second thrust bearing 41 are also contemplated. For example, an annular thrust bearing surface could be provided on the inner wall of casing 14, adjacent the upper face portion 36 of impeller 19. In this arrangement, portion 36 would slidably, contact the annular thrust bearing surface. By eliminating spider 46 and the associated components of the upstream thrust bearing, the possibility of blood deposits forming on these structures would be eliminated.

It will be appreciated that thrust bearings 39 and 41 are effective not only to provide limit stops to axial movement of rotor 17, but also to adjust certain operational aspects of the pump. In the drawings, the upstream end of support shaft 18 is shown in contact with ball 48. However, this will not always be the case during the course of operating the pump. For example, it is desirable for the two thrust bearings to be adjusted so that the distance between them is slightly greater than the overall length of the rotor. This will allow the rotor to "shuttle" back and forth between the axial constraints provided by the thrust bearings with each cardiac cycle of the user. Each such cycle will produce a pumping action, bringing fresh blood into the touchdown, or thrust bearing area.

The present invention typically does not use a journal bearing to restrain the rotor. Of necessity, a journal bearing radially encases at least a portion of the rotor's support shaft or spindle. It is within this thin, annular volume between the shaft and the bearing surface, where thrombosis can occur in prior art devices as a consequence of heat and excessive residence time within the bearing. The bi-stable operation of the pump and rotor of the present invention, continuously flushes the blood around each thrust bearing, avoiding thrombosis effects of prior art journal bearings.

There is also an important physical relationship which exists between the rotor and the magnetic bearings of the device disclosed herein. This relationship is established and maintained by proper axial placement of the adjustable thrust bearings. In operation of the pump, the pressure gradient produced by the rotating impeller imparts an upstream axial force on the rotor. This force needs to be substantially counterbalanced, to ensure that cardiac pulses will create sufficient pressure variances through the pump, to effect bi-stable operation. By adjusting the axial relationship of the pole pieces 23 and the magnets 24 with respect to the pole pieces 28 and magnets 29, a downstream axial force will be produced. Since the forces within forward magnetic bearing 21 are repulsive, the desired downstream loading or bias will be effected when the magnets and pole pieces within the shaft are translated slightly downstream from the magnets and pole pieces in the inlet tube (See FIGS. 7 and 8). Thus, second thrust bearing 41 is effective to shift, or offset, the rotor downstream a sufficient amount so the resultant, repulsive magnetic forces substantially counterbalance the hydrodynamic axial force produced by the rotating pump impeller.

We can now turn to the special design considerations and operational characteristics of impeller 19. As will be noted particularly in FIG. 6, the impeller includes a plurality of large blade sectors 49. Owing to its relatively high viscosity and susceptibility to damage from heat and mechanical action, blood is a uniquely difficult liquid to pump.

It is generally preferable in a large centrifugal pump, to have a substantial number of thin, sharp impeller blades with relatively large voids or passages, between the blades, for the passage of low viscosity liquid. However, such a conventional design is not desirable, for a small centrifugal pump which has to pump a viscous liquid, such as blood.

When blood flows axially into the leading edges of impeller blades it tends to be damaged by the mechanical action and turbulence associated with the impeller blades. Thus, one of the design considerations of the present invention is to reduce such hemolysis, by minimizing the number of impeller blades and leading edges.

To maintain efficiency in a small pump with so few blades, the effective working area of the blades needs to be increased. This was accomplished in the present design by modifying the size and configuration of conventional blades in two significant aspects. First, blade sectors 49 are made relatively wide or expansive through a rotational aspect (see FIG. 6). In other words, the outer periphery of each blade sector 49 assumes approximately 80 to 85 degrees of rotation. It should be noted that an alternative design contemplated herein includes only two blade sectors, each of which assumes approximately 175 degrees of rotation. In either case, the width of the impeller blade sectors in this embodiment differs significantly from known prior art blades.

The second modification pertains to the thickness or height of the blade sectors. As shown particularly in FIGS. 4 and 7, blade sectors 49 are relatively thick in an axial direction. As a consequence of these modifications, a narrow and deep impeller blood flow path or passageway 51 is defined between adjacent edges of blade sectors 49. By increasing the thickness of the blade sectors and narrowing the blood passageway, the ratio between the area of working surface of the blades and the volume of the passageway is increased. Also, the average distance of the liquid in the passageway from the working surface of the blades is decreased. Both of these beneficial results provide a small pump for blood which has few blades for damaging blood, yet maintains acceptable efficiency.

The size and configuration of the impeller blades also allows the structural integration of a number of features directly within the impeller 19. For example, the previously discussed rearward magnetic bearing 22 includes a plurality of rod magnets 34 of considerable length. Owing to the thickness of the blade sectors, these magnets are readily accommodated within the sectors. The sectors may also be provided with respective hollow chambers 52, to reduce the mass of the impeller and the gravity induced loads on the thrust bearings (see FIG. 6).

Figure 1:
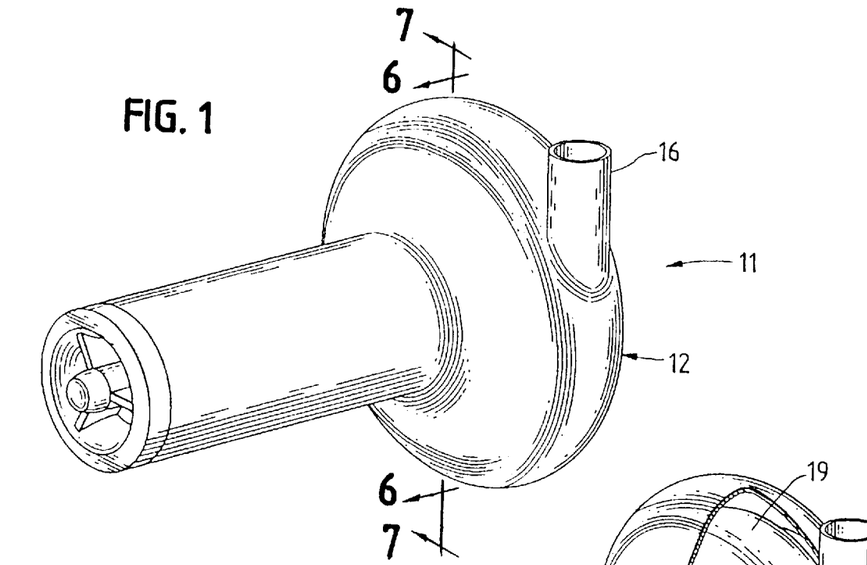
FIG. 1 is a left front perspective of a blood pump of the present invention.
Figures 2, 3:
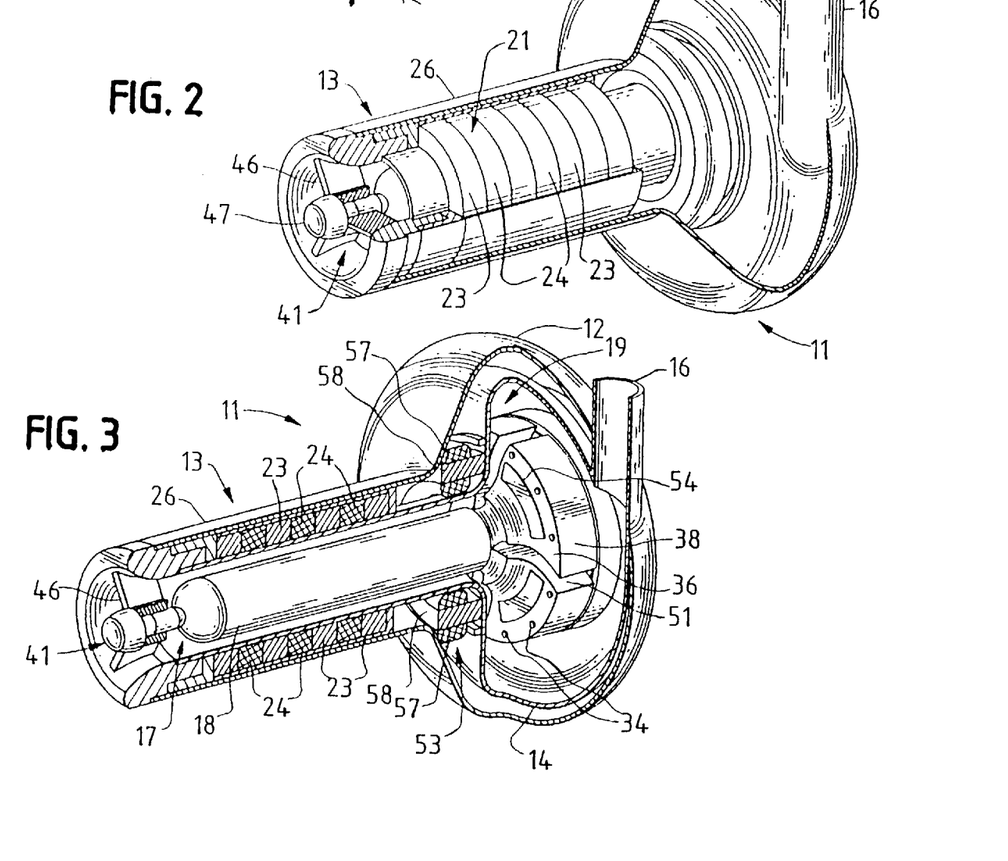
FIG. 2 is a fragmentary, cross-sectional view of the pump of FIG. 1, showing a plurality of ring magnets comprising part of the magnetic bearing assembly.
FIG. 3 is a fragmentary, cross-sectional view of the pump of FIG. 1, showing the shaft and an impeller.
Figure 4:
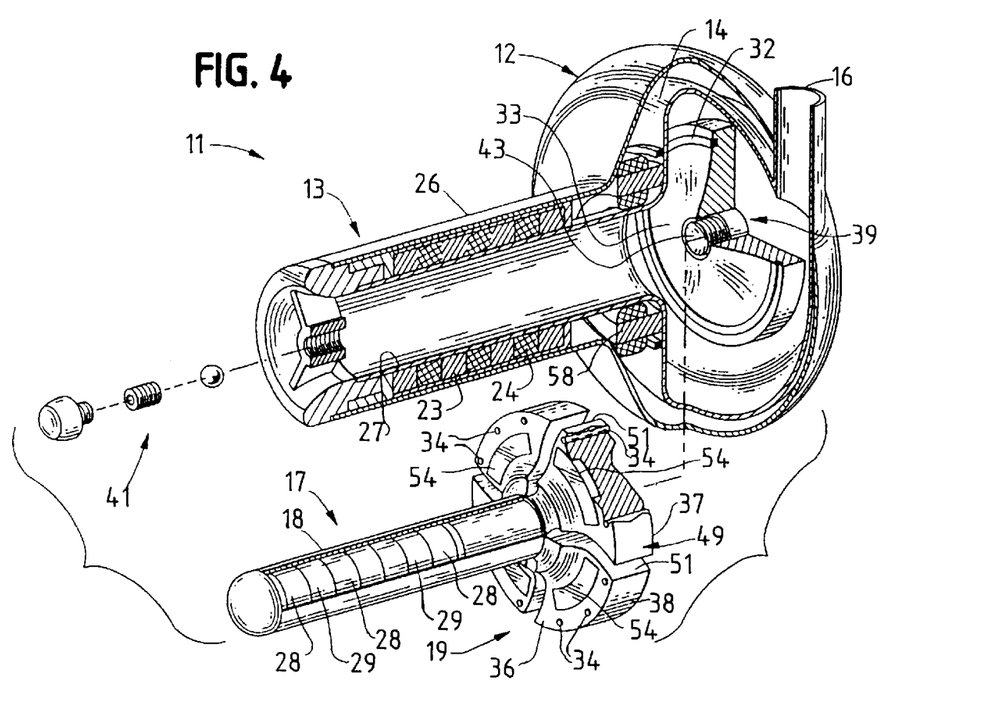
FIG. 4 is a view as in FIG. 1, but with the shaft and impeller shown removed from the housing.
Figure 5:
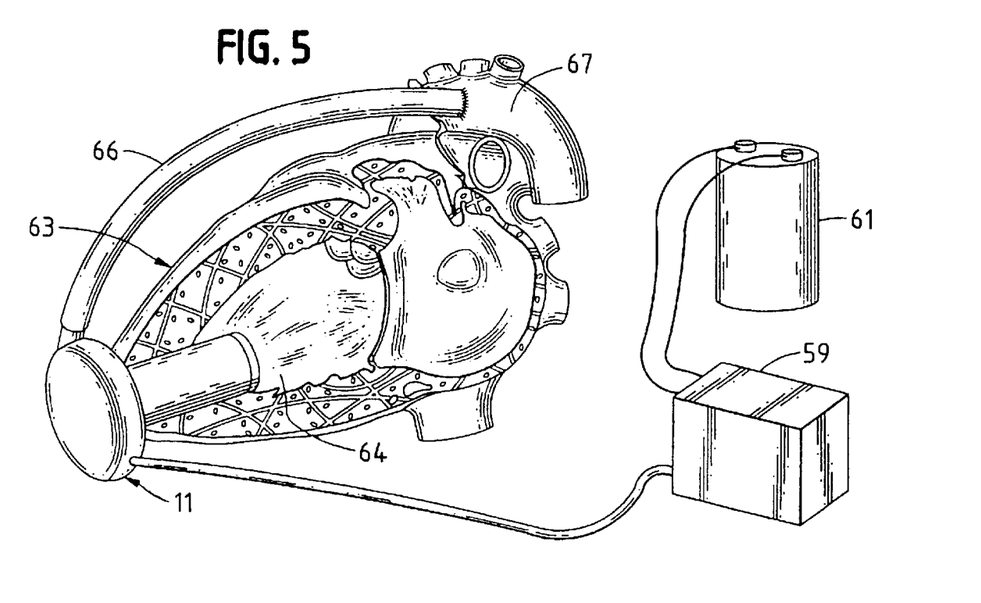
FIG. 5 is a simplified, fragmentary, representation of a human heart, showing the pump implanted within the left ventricle of the heart.
Figure 6:
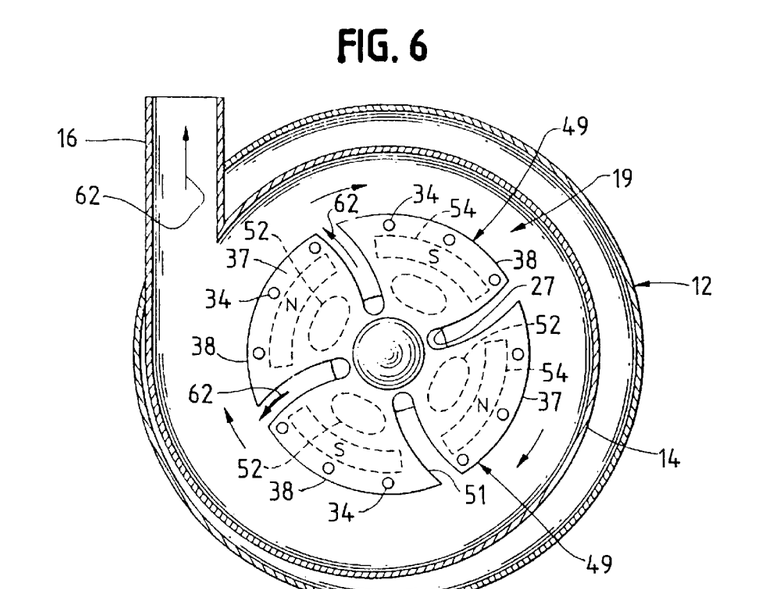
FIG. 6 is a transverse, cross-sectional view of the housing, impeller, and impeller chamber, taken along the line 6—6, shown in FIG. 1.

Lastly, a brushless rotor motor 53 includes arcuate magnetic segments 54, imbedded within the upper face portion 36 of blade sectors 49. As discussed above, the portions of segments 54 which would otherwise be in fluid communication with the pumped blood, are encased in a jacket or a coating (not shown) to prevent any chemical reaction between the blood and the magnetic segments. Making reference to FIGS. 6 and 8, segments 54 have alternating orientations in their polarities, and are directed toward an adjacent motor stator 56. Included within stator 56 are windings 57 and a circular pole piece or back iron 58, mounted on the outer surface of impeller casing 14. Windings 57 are interconnected by means of percutaneous wires to a controller 59 and a power supply 61, as shown in FIG. 5. Alternative to using wires, transcutaneous power transmission could be used. It is contemplated that controller 59 and power supply 61 may be worn externally by the user, or alternatively, they may be completely implanted in the user.

Controller 59 may include circuitry as simple as a variable voltage or current control, manually adjusted or programmed to determine the running rate of pump. However, controller 59 may also have interactive and automatic capabilities. For example, controller 59 may be interconnected to sensors on various organs of the user, automatically and instantaneously to tailor operation of the pump to the user's physical activity and condition.

The windings 57 are energized by the electrical output of controller 59 to produce an electromagnetic field. This field is concentrated by pole piece 58, and is effective to drive magnets 54 and the rotor 17, in rotary fashion. The back EMF resulting from the magnets 54 passing by the windings is detected by the controller. The controller uses this back EMF voltage to continue generation of the electromagnetic field in synchronism with further rotation of the rotor. Brushless operation of the motor 53 is effected, then, by electromagnetic interaction between the stator and magnets imbedded within the pump's impeller blades.

Figure 7:
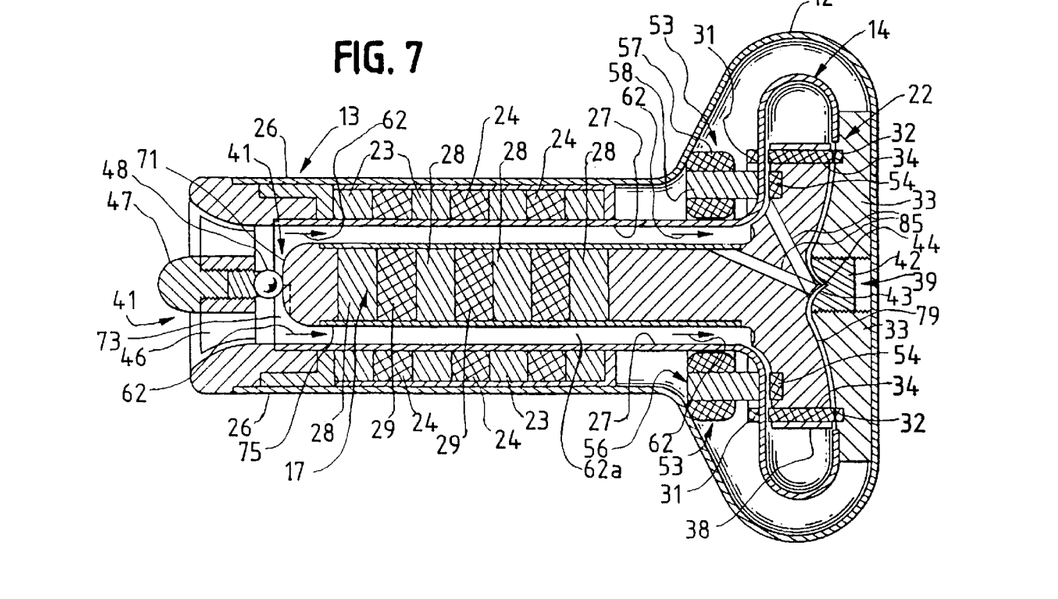
FIG. 7 is a longitudinal, cross-sectional view of the pump, taken along the line 7—7, shown in FIG. 1.
Figure 8:
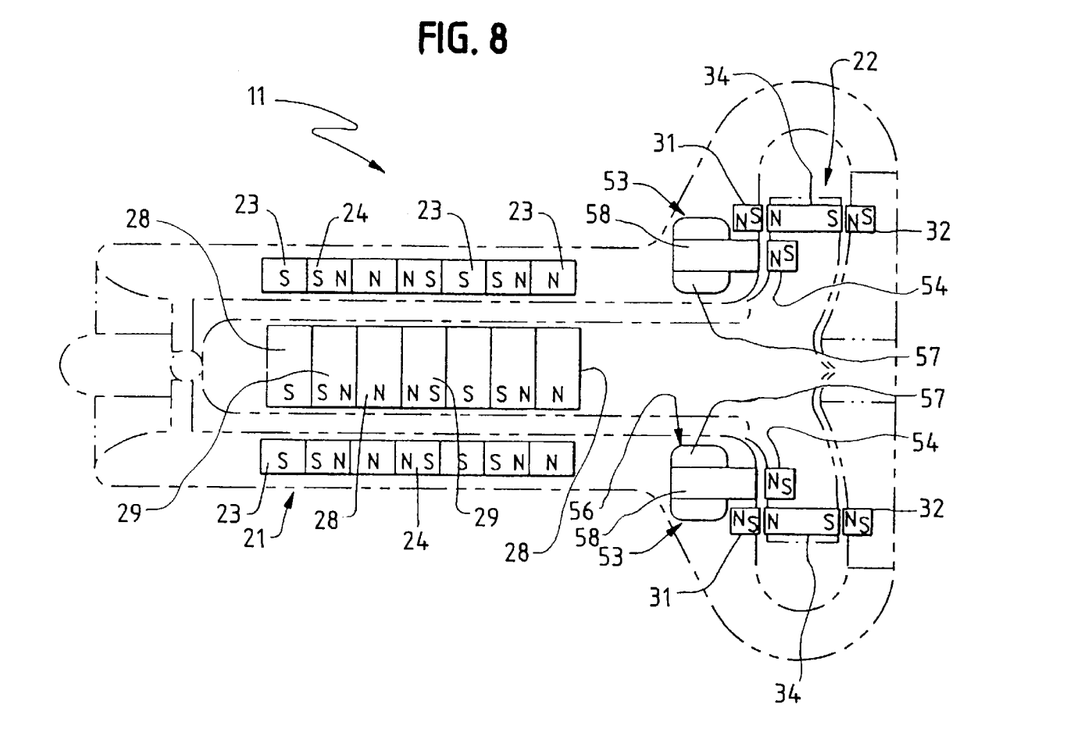
FIG. 8 is a longitudinal, cross-sectional view of a simplified, schematic representation of the pump, showing respective polarities of the magnets and the pole pieces of the passive radial magnetic bearings, and the elements of the pump motor, including rotor magnets and a motor stator.

Motor 53, with windings 57 and pole piece 58, together with magnets 54, function not only to transmit torque but also provide a restoring radial magnetic force that acts as a radial bearing. As illustrated in FIGS. 7 and 8, magnets 54 are carried by blade sectors 49 and are positioned in radial alignment with pole piece 58. The magnets 54 have attraction with the iron pole piece 58 of the stator. Any attempt to deflect the impeller radially produces an increasing restoring force between the pole piece 58 and the magnets 54 which would cause the impeller to return to a neutral position.

Rotation of the rotor 17, including shaft 18 and impeller 19, causes blood to flow through inlet tube 13 in the direction of arrows 62. The blood continues its path from the upper edge of passage 51 to the interior of casing 14. Discharge tube 16 allows the blood to be expelled from the casing and into the user's cardiovascular system.

Anatomical placement of the pump 11 is shown in FIG. 5. The simplified representation of a human heart 63, includes a left ventricle 64 and an aorta 67. The inlet tube 16 serves as the inflow cannula and is placed into the apex of the left ventricle 64. An arterial vascular graft 66 is connected on one end to tube 16 and on the other end to the aorta 67 through an end to side anastomosis.

The centrifugal design of the pump allows a considerable amount of flexibility during implantation. Owing to the axial inflow and radial outflow of the pump, a 90 degree redirection of the blood is effected without the necessity of a flow-restrictive elbow fitting. Moreover, the pump can be rotated on its longitudinal axis to adjust the orientation of the discharge tube and minimize kinking and hydraulic losses in the vascular graft. Good anatomic compatibility is possible since the pump casing is compact and disc-shaped, fitting well between the apex of the heart and the adjacent diaphragm.

Figures 9, 10, 11:
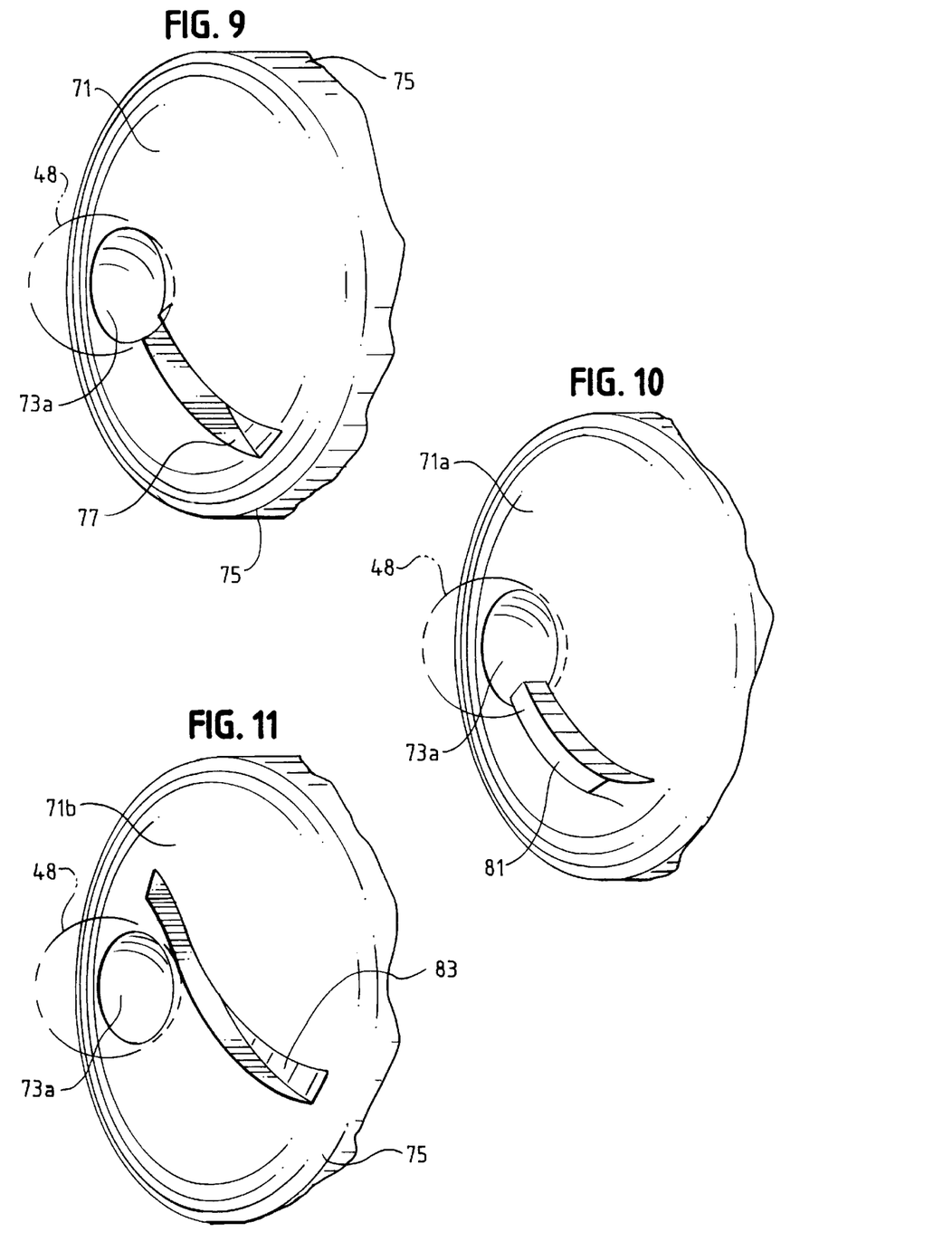
FIGS. 9, 10 and 11 each respectively show different embodiments of end faces for the thrust bearing at an end face of the rotor shown in FIGS. 1 through 8, which end face defines the profiled surface of this invention.

In accordance with this invention, FIG. 9 shows one embodiment of the end face 71 of pump rotor 17 as it interacts with ball 48 to form thrust bearing 41. It can be seen that a narrow, annular space 73 (FIG. 6) is defined around ball 48 in the vicinity of end face 71, which comprises an area where blood can collect under stagnant conditions even when the rotor 17 of the pump is rotating as taught above. Rotor 17 can shuttle back and forth along its longitudinal axis during operation, causing blood circulation, but it is often desirable for greater circulation of blood into and out of annular space 73 to be provided.

By this invention, end face 71 defines a profiled surface that augments blood flow radially outwardly from central portion 73a of the rotor face (which may be a recess that engages ball 48) toward and across peripheral edge 75 of rotor 17.

Specifically, the profiled surface comprises a channel 77 extending from central portion 72 of end face 71 in substantially radial direction outwardly toward peripheral edge 75, being open at the peripheral edge so as to extend thereacross. Thus, as rotor 17 rotates, blood from stagnant area 73 is collected in channel 77 and is urged outwardly by the rotation of channel 77 to flow across peripheral edge 75, thus creating an improved circulatory flow pattern of blood in the area of annular space 73.

By this simple expedient, a greatly increased circulatory flow of blood can take place at the end or the respective ends of rotor 17. Specifically, a similar profiled surface and particularly a channel of similar type can be provided in end face 79 of rotor 17, opposed to end face 71, to create a similarly increased flow of blood out of the stagnant space adjacent to end face 79 and thrust bearing 39.

Referring to FIG. 10, an alternate design for end face 71, labelled end face 71a, is shown. Here, the profiled surface of the end face comprises a rib 81 rather than a channel, with rib 81 extending along substantially the same path as channel 77 of the prior embodiment of FIG. 9. As rotor 17 of the pump rotates, rib 81 creates a circulatory flow of blood within space 73, which urges outward flow of the blood which, in turn, results in a circulatory flow pattern of blood through annular area 17 to substantially reduce stagnation and the resulting tendency for blood to clot in area or space 73. Here also, face 79 (FIG. 7) of the rotor may be similarly modified to achieve an equivalent result.

Referring to FIG. 11, another embodiment of end face 71 for rotor 17 is shown, being identified as end face 71b. The profiled surface of this face comprises a channel 83 which extends from a central portion of face 71b toward and across peripheral edge 75 of rotor 17 as in previous embodiments, but this embodiment does not extend directly toward the center of face 71b and thus is less radial in extent. However, channel 83 still collects blood from a central area of the rotating face 71b and urges it radially outwardly across peripheral edge 75 of the rotor in a continuous flow as the rotor is operating in pumping action.

Accordingly, each of the embodiments of FIGS. 9–11 cause an increase in the replacement of blood through annular space 73, which reduces stagnancy and the consequent tendency of blood to clot.

A profiled surface similar to that shown in FIG. 11 may be applied to end face 79 of rotor 17, for similar beneficial effect.

To further facilitate circulation of blood across a rotor end face such as end face 79, one or more conduits such as drill holes 85 may be provided, extending through a central portion of end face 79 and communicating through a surface of the rotor that is spaced from the end face. Thus, blood circulation from the constricted area adjacent to end face 79 can be further enhanced by the presence of such conduits, which may be formed as drill holes.

If desired, plug 42 may be replaced with an electromagnet or a permanent magnet to serve as a magnetic bearing in which rotor 17 is held in spaced relation therefrom by magnetic force.

In a specific example, although no limitation is intended, referring to FIG. 7, blood flow path 62a is 0.06 inch to 0.1 inch in thickness. The fluid gap 70 comprising the clearance between the impeller and the housing is 0.005 inch to 0.02 inch. The impeller diameter is 1.0 inch to 1.5 inch. The rotor diameter is 0.25 inch to 0.4 inch. The outside diameter of the flow annulus is 0.35 inch to 0.55 inch. The outer diameter of the housing adjacent the forward end of the pump is 0.85 inch to 1.25 inch. The axial length of the entire pump is 1.75 inch to 3.0 inch. The axial length of the rotor spindle is 1.0 inch to 1.5 inch and the axial length of the impeller is 0.2 inch to 0.5 inch. By using a thick impeller (having a long axial length) the fluid gap 70 can be larger and still provide a highly efficient pumping action.

Figure 12:
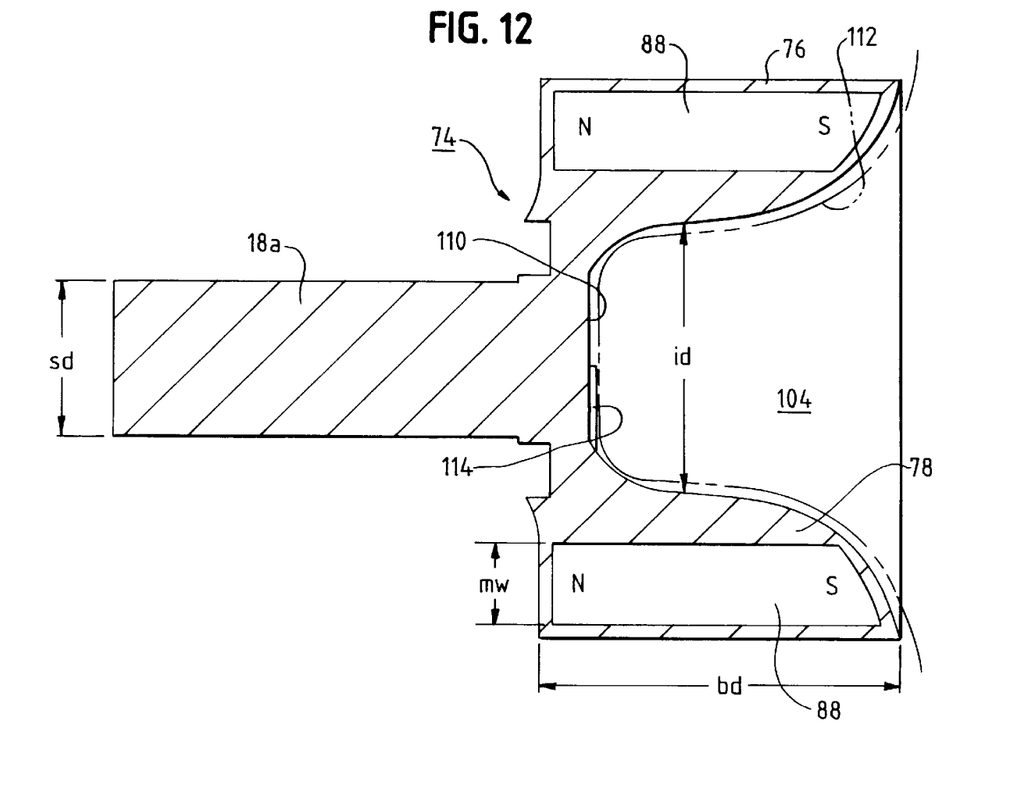
FIG. 12 is a longitudinal, cross-sectional view of an impeller constructed in accordance with the principles of the present invention.
Figure 13:
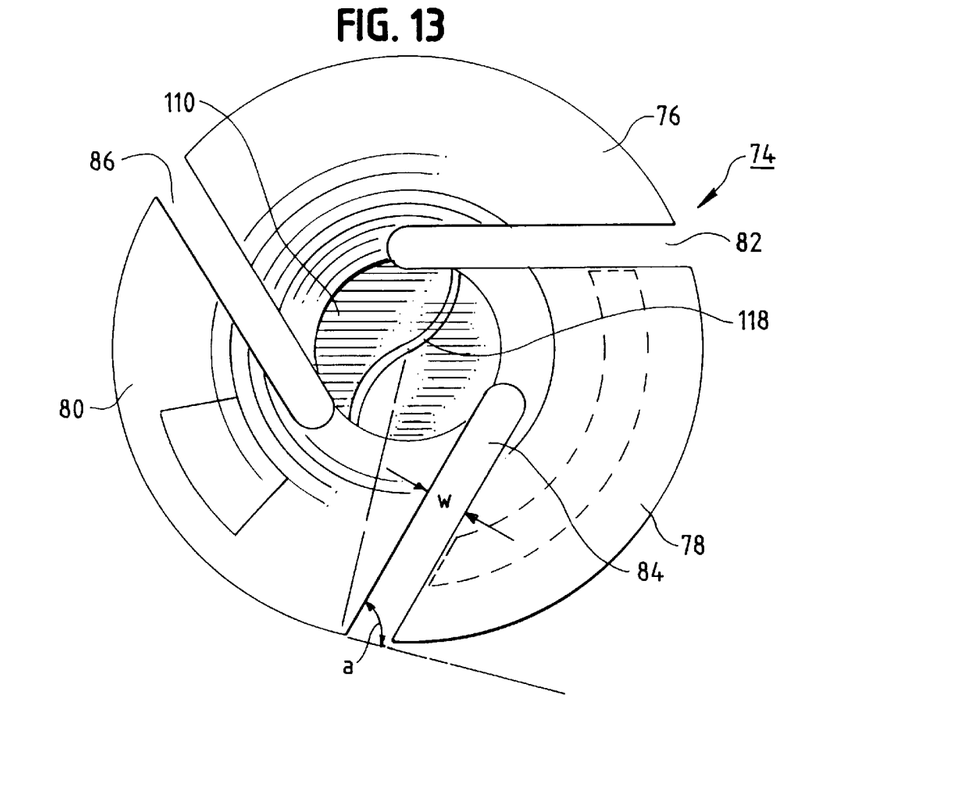
FIG. 13 is an end view thereof, taken from the right side of FIG. 12.

Enlarged views of another design of impeller used in the pump of the present invention are set forth in FIGS. 12 and 13. Referring to FIGS. 12 and 13, an impeller 74 is shown therein having a number of blade sectors 76, 78 and 80. Blade sectors 76 and 78 are separated by slot 82; blade sectors 78 and 80 are separated by slot 84; and blade sectors 80 and 76 are separated by slot 86. By utilizing blade sectors 76, 78 and 80 that are relatively thick in the axial direction, narrow and deep impeller blood flow paths are formed by slots 82, 84 and 86 between the adjacent edges of the blade sectors. By increasing the thickness of the blade sectors and narrowing the blood passageway, the ratio between the area of working surface of the blades and the volume of the passageway is increased. Also, the average distance of the liquid in the passageway from the working surface of the blades is decreased. Both of these beneficial results allow a small pump for blood which has less blades for potentially damaging blood, yet the small pump maintains acceptable efficiency.

As a specific example although no limitation is intended, the diameter of the impeller is 1 inch to 1.5 inch, the blade depth bd (FIG. 12) is 0.2 inch to 0.5 inch, the magnet width mw (FIG. 12) is 0.15 inch to 0.3 inch the spindle diameter sd (FIG. 12) is 0.25 inch to 0.5 inch, and the inner diameter id (FIG. 12) of the impeller inlet is 0.45 inch to 0.6 inch. The width w of the slots (see FIG. 13) is approximately 0.075 inch and preferably ranges from 0.05 inch to 0.2 inch. The outlet angle a (FIG. 13) preferably ranges between 30° and 90°.

Figure 14:
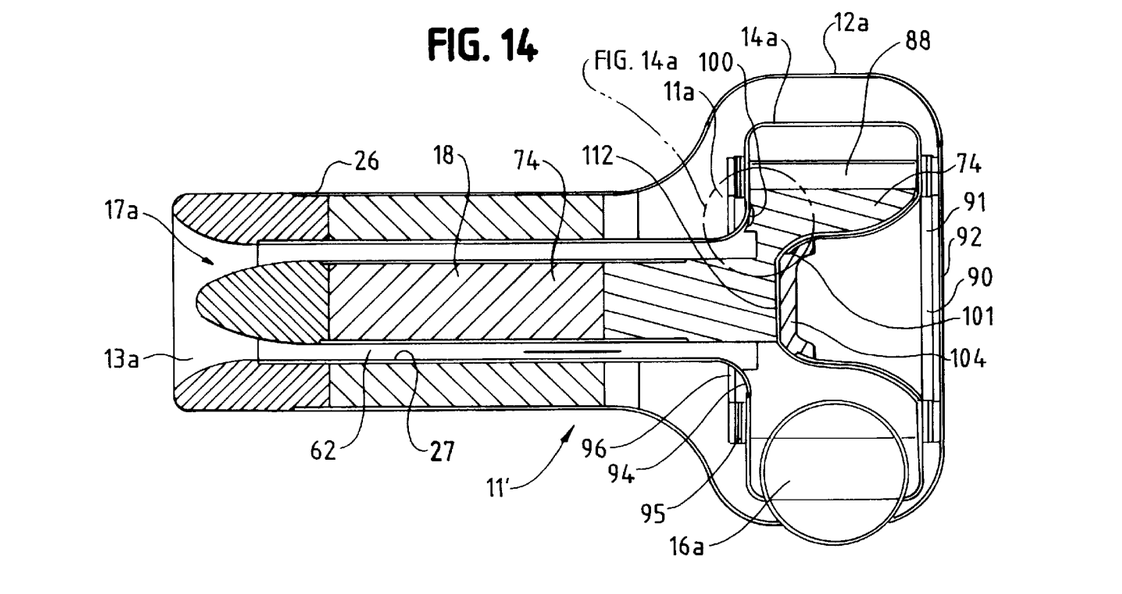
FIG. 14 is a longitudinal, cross-sectional view of a simplified, schematic representation of another embodiment of the pump, using an impeller similar to that of FIGS. 12–13.
Figure 15:
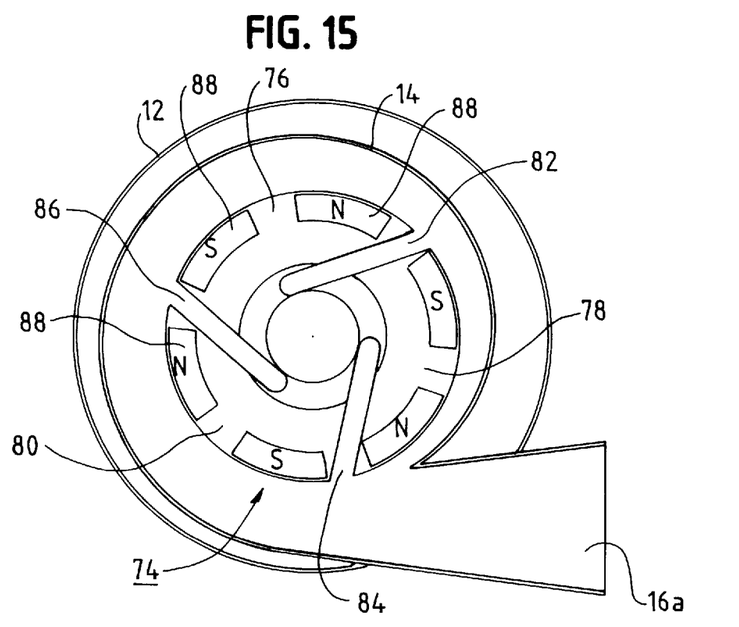
FIG. 15 is a cross-sectional end view of the FIG. 11 pump with the end of the housing and casing removed for clarity.

Another benefit of the thick impeller is the ability to utilize magnetic pieces 88 that are inserted in a manner enabling the stators to be on opposite sides of the impeller 74. Referring to FIGS. 14–15, the blood pump 11 shown therein is similar in many respects to blood pump 11 illustrated in FIGS. 1–11, and includes housing 12a having an elongated inlet tube 13a and a scroll-shaped impeller casing or volute 14a. A discharge tube 16a extends through the housing to communicate with the interior periphery of casing 14a. Tube 16a has a tangential orientation with respect to a radius of the casing, for effectively channeling the blood output from the pump.

Pump rotor 17a is located within housing 12, within casing 14, and includes an elongated, right-circular cylindrical support shaft or spindle 18, attached to impeller 74. Rotor 17a is mounted for rotation about an longitudinal axis which extends both through shaft 18a and impeller 74.

The magnetic bearings for levitating rotor 17a and maintaining it in proper radial alignment with respect to its longitudinal axis are not specifically shown but may be identical to those illustrated in the pump embodiment of FIGS. 1–8 and described above.

In the FIGS. 14–15 embodiment, a first motor stator 90, comprising conductive coils or motor windings 91, is located at the rear of impeller 74. A ring of back iron 92 is located behind windings 91 and, as illustrated, first motor stator 90 and back iron 92 are fixed between housing 12a and casing 14a.

A second motor stator 94, comprising windings 95, is positioned on the forward side of impeller 74. As illustrated in FIG. 14, windings 95 are fixed to casing 14a and a ring of back iron 96 is positioned forward of windings 95. Further details are found in the previously cited application Ser. No. 08/910,375.

The motor stators 90 and 94 are placed on opposite sides of casing 14 such that each is adjacent to the pole faces of motor rotor magnets 88. Back iron 92 and back iron 96 serve to complete a magnetic circuit. The windings 91 and 95 of the stators 90, 94 can be in series or each stator 90, 94 can be commutated independent of the other. There are several advantages to this approach:

First, as long as the pole faces of the motor rotor magnets are centered between the faces of the motor stators, the net axial force will be relatively low.

Second, the radial restoring force which results from the attractive force of the motor rotor magnets to the motor stators will be nearly twice as large as the restoring force with only one stator. The total volume and weight of the motor will be smaller than a single stator design.

Third, the dual stator design is adapted to provide system redundancy for a fail safe mode, since each stator can be made to operate independently of the other in the case of a system failure.

Figure 14A:
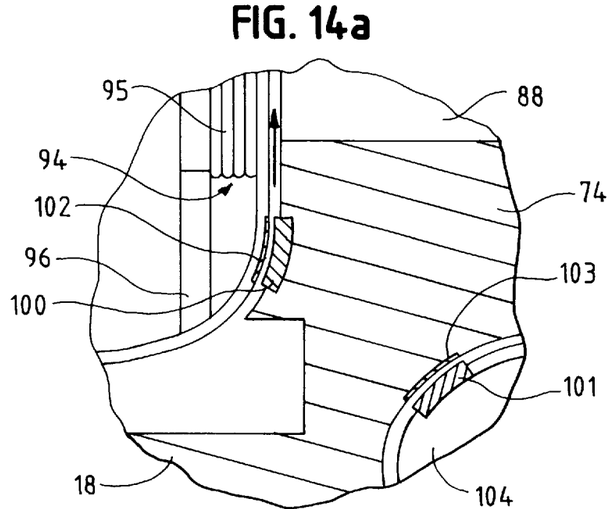
FIG. 14a is an enlarged view of the circled portion 11a from FIG. 14.

Fourth, hydrodynamic bearings can be located on the surface of the impeller to constrain axial motion and to provide radial support in the case of eccentric motion or shock on the device. Referring to FIGS. 14 and 14a in particular, hydrodynamic bearings in the form of raised pads 100, 101 and contact surfaces 102 and 103 are illustrated. Such hydrodynamic bearings are symmetrically located about the impeller.

The raised pads could be rectangularly-shaped or wedge-shaped and are preferably formed of hardened or wear resistant materials such as ceramics, diamond coatings or titanium nitride. Alternatively, the raised pads may be formed of a different material having an alumina or other ceramic coating or insert.

The raised pads are carried by either the impeller or the casing, or an attachment to the casing. In the FIGS. 14 and 14a embodiment, the raised pads 100 are carried by the impeller and the raised pads 101 are carried by a cup-shaped member 104 that is fastened to the casing. Cup-shaped member 104 is utilized as a reinforcement for the casing which would not be structurally stable enough to carry the raised pads itself.

The hydrodynamic bearings are formed by a raised pad spaced from a contact surface by the blood gap. Although at rest there may be contact between the impeller and the casing, once rotation begins each hydrodynamic bearing is structured so that during relative movement between the raised pad and the contact surface the hydrodynamic action of the fluid film produces increased pressure within the bearing gap which forces the raised pad and the contact surface apart.

Depending upon the location of the hydrodynamic bearings, they can aid in axial support, radial support or both axial and radial support. For example, if the bearings are perpendicular to the rotational axis, they aid primarily in axial support but if they are at an angle with respect to the rotational axis, they aid in both radial and axial support. In the embodiment of FIGS. 14–15, the hydrodynamic bearings are positioned outside the axis of rotation, as illustrated.

In accordance with this invention, the rotor end face 110 is recessed as shown particularly in FIG. 12. This end face is part of cup-shaped member 104 of the casing, with a relatively narrow, cup-shaped space 112 between cup shaped member 104 and rotor 74, which space fills with blood. By this invention, improved circulation of blood through this cup-shape space 112 is provided by means of profiling 114 of recessed end face 110 (FIG. 12).

Figures 16, 17, 18:
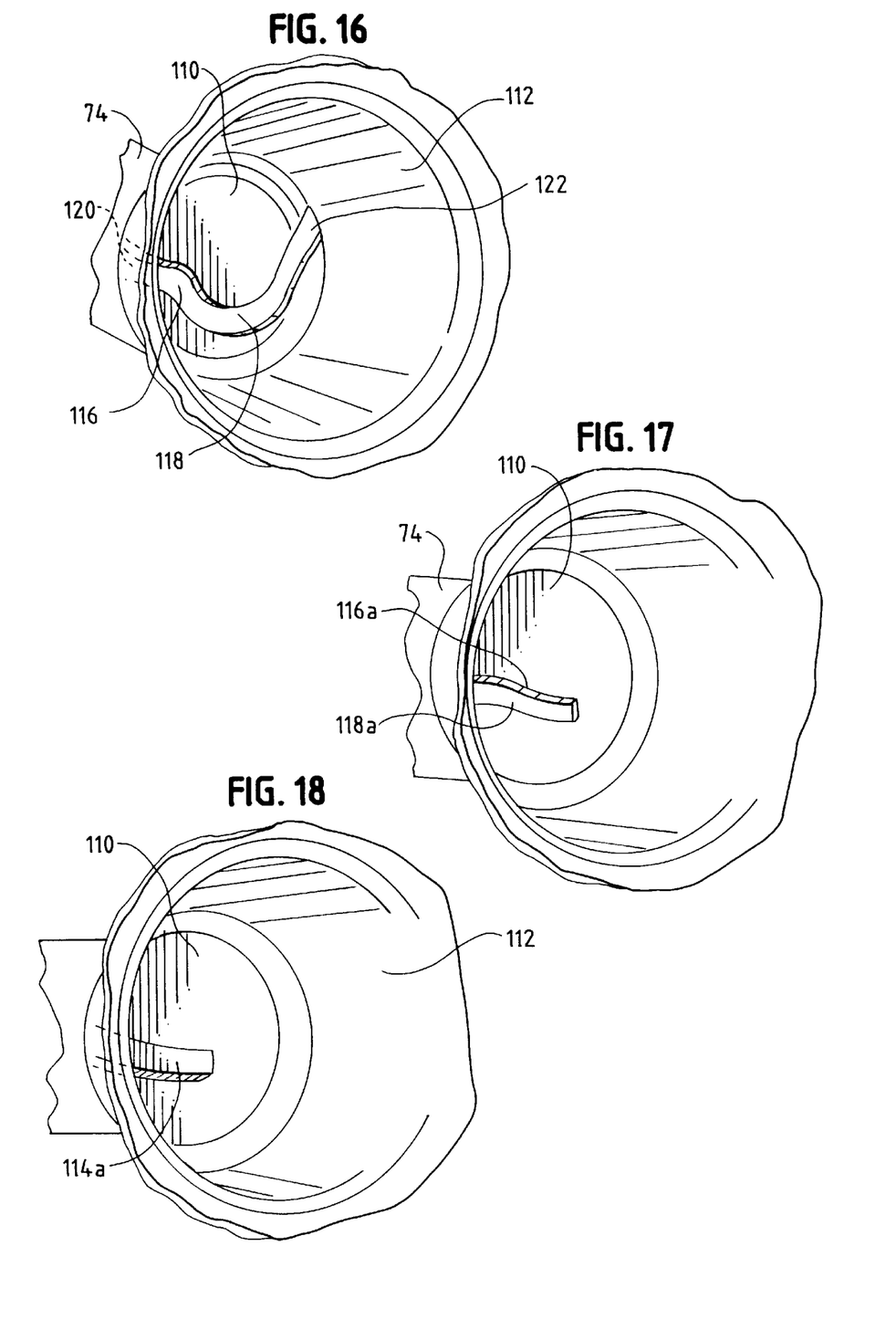
FIGS. 16, 17 and 18 each respectively show different embodiments for the central end face portion of the impeller of the pump of FIG. 12, showing different embodiments for the profiled surface of this invention.

The profiling of end face 110 is shown in the FIG. 16 embodiment to comprise a channel 116 in end face 110 which extends outwardly in a plurality of directions toward the peripheral edge of the end face from the central portion 118 of the end face. It can also be seen that the angle that segment 120 of channel 118 directs its radially outer end toward the edge of the end face is different from the corresponding angle of segment 122 of channel 118, resulting in differing flow characteristics of the respective channel ends. The angle of segment 120 is about 90°; the angle of segment 122 is about 60°

Channel 118 is shown as a specific embodiment of possible profiling of recessed end face 110 in FIG. 13, with this profiling being different from that shown in FIG. 12, for purposes of broader illustration.

Referring to FIG. 17, another embodiment of profiling for end face 110 is shown as channel 118a. This channel extends from a central portion 116a of the end face substantially radially outwardly toward an edge thereof. Blood in channel 118a is driven outwardly by the rotating end face 110 and channel 118a, as part of the rotor 74 during operation of the pump.

FIG. 18 shows a third embodiment for the profiling of end face 110. This particular profiling 114a may be similar to that shown in FIG. 12, comprising a substantially radial projection that extends from the center of recessed end face 110 out to the edge thereof.

Thus, as the rotor rotates, bar 114a of the profiling sweeps in a 360° arc about the bottom portion 110 of the cup-like space 112, causing outward flow circulation of blood, which provides a continuous circulation and motion of blood throughout cup-like space 112, for the suppression of clotting.

Although illustrative embodiments of the invention have been shown and described, it is to be understood that various modifications and substitutions may be made by those skilled in the art without departing from the novel spirit and scope of the present invention.

That which is claimed:

1. A blood pump comprising: a pump housing, a rotor mounted for rotation within said housing, said rotor having a rotational axis and an attached impeller, said blood pump having a blood flow path that passes about said rotor, said rotor having a peripheral edge surrounding an end face, said end face having a profiled surface that is nonperiodic with respect to said rotational axis, to augment blood flow radially outwardly from a central portion of said end face toward the peripheral edge as said rotor rotates, when compared with a flat end face.

2. The blood pump of claim 1 in which said profiled surface comprises a channel extending from said central portion of said end face outwardly toward said peripheral edge.

3. The blood pump of claim 2 in which said channel extends outwardly in a plurality of directions toward said peripheral edge from said central portion of the end face.

4. The blood pump of claim 3 in which said channel engages said peripheral edge in at least a pair of spaced positions, the channel at a first of said positions defining an angle with said peripheral edge which is different from the angle between said channel and the peripheral edge at a second of said positions.

5. The blood pump of claim 2 in which said channel has a closed end at said central portion of the end face.

6. The blood pump of claim 2 in which at least one conduit extends through said rotor between the channel and a surface of said rotor that is spaced from the end face, to enhance blood circulation across said end face.

7. The blood pump of claim 1 in which said profiled surface comprises a projecting rib extending from a central portion of said end face outwardly toward said peripheral edge.

8. The blood pump of claim 1 in which said pump housing comprises an elongated inlet tube at one end and an impeller casing portion on another end, said casing portion including a discharge tube.

9. The blood pump of claim 8 in which said rotor has an elongated shaft portion, said impeller being attached to said shaft portion at a position located within said impeller casing portion.

10. The blood pump of claim 1 in which said end face defines a thrust bearing for restraining said rotor from translating past a predetermined position along its axis, said thrust bearing comprising mating bearing surfaces respectively carried by said rotor and said pump housing, said profiled surface comprising a channel extending within said thrust bearing from said central portion of said end face outwardly across said peripheral edge.

11. The blood pump of claim 1 in which a motor stator within said housing is positioned adjacent the impeller for producing an electromagnetic field.

12. The blood pump of claim 1 in which said profiled surface of the end face defines a flow recess occupying a position that at least nearly intersects said rotational axis, said recess permitting radially outward flow in said recess as the rotor rotates.

13. A sealless blood pump, comprising:

a pump housing having an elongated inlet tube on one end and an impeller casing on another end, said casing including a discharge tube;

a rotor mounted for rotation within said housing, said rotor having an elongated shaft portion having a rotational axis and an impeller attached to said shaft portion, said impeller being located within said impeller casing; a primary flow channel for blood being provided by an annular volume between said shaft portion and housing;

a thrust bearing for restraining said rotor from translating past a predetermined position along its axis, said thrust bearing comprising mating bearing surfaces respectively carried by said rotor and said pump housing; a motor rotor carried by said impeller; and a motor stator within said housing adjacent a surface of said impeller, for producing an electromagnetic field;

said bearing surface of the rotor defining a flow recess occupying a position that at least nearly intersects said rotational axis, said recess extending radially outwardly from said rotational axis across a radially outer boundary of said thrust bearing, said recess being nonperiodic with respect to the rotational axis, permitting radially outward flow in said recess as the rotor rotates.

14. The blood pump of claim 13 in which said flow recess comprises a channel from a central portion of said bearing surface outwardly toward a peripheral edge of said bearing surface.

15. The blood pump of claim 14 in which said channel extends outwardly in a plurality of directions toward said peripheral edge from said central portion.

16. The blood pump of claim 15 in which said channel engages said peripheral edge in at least a pair of spaced positions, the channel having a first of said positions defining an angle with said peripheral edge which is different from the angle between said channel and the peripheral edge at a second of said positions.

17. The blood pump of claim 13 in which said channel has a closed end at a central portion of the thrust bearing.

18. A sealless blood pump, comprising:

a pump housing;

a rotor mounted for rotation within said housing, said rotor having an impeller with a rotational axis;

a thrust bearing for restraining said rotor from translating past a predetermined position along its axis, said thrust bearing comprising mating bearing surfaces respectively carried by said rotor and said pump housing;

said bearing surface of the rotor defining a flow recess occupying a position that at least nearly intersects said rotational axis, said recess extending radially outwardly from said rotational axis across a radially outer boundary of said thrust bearing, said recess being nonperiodic with respect to said rotational axis, permitting radially outward flow in said recess as the rotor rotates.

19. The blood pump of claim 18 in which said flow recess comprises a channel extending from a central portion of said flow recess outwardly toward a peripheral edge of said thrust bearing.

20. The blood pump of claim 19 in which said channel extends outwardly in a plurality of directions toward the peripheral edge from said central portion.

* * * * *